US010767244B2

(12) United States Patent
Wolter et al.

(10) Patent No.: US 10,767,244 B2
(45) Date of Patent: Sep. 8, 2020

(54) TITANIUM ALLOY

(71) Applicant: Dietmar Wolter, Hoisdorf (DE)

(72) Inventors: Dietmar Wolter, Hoisdorf (DE);
Carsten Siemers, Braunschweig (DE);
Heinz Sibum, Grevenbroich (DE)

(73) Assignee: Dietmar Wolter, Hoisdorf (DE)

( * ) Notice: Subject to any disclaimer, the term of this patent is extended or adjusted under 35 U.S.C. 154(b) by 223 days.

(21) Appl. No.: 15/324,192

(22) PCT Filed: Jun. 22, 2015

(86) PCT No.: PCT/DE2015/100252
§ 371 (c)(1),
(2) Date: Jun. 16, 2017

(87) PCT Pub. No.: WO2016/004918
PCT Pub. Date: Jan. 14, 2016

(65) Prior Publication Data
US 2017/0314099 A1 Nov. 2, 2017

(30) Foreign Application Priority Data

Jul. 8, 2014 (DE) .................. 10 2014 010 032

(51) Int. Cl.
C22C 14/00 (2006.01)
C22F 1/18 (2006.01)
A61L 27/06 (2006.01)

(52) U.S. Cl.
CPC .............. *C22C 14/00* (2013.01); *A61L 27/06* (2013.01); *C22F 1/183* (2013.01)

(58) Field of Classification Search
CPC .......................... C22C 14/00; C22F 1/183
See application file for complete search history.

(56) References Cited

U.S. PATENT DOCUMENTS

| 4,886,559 | A | * | 12/1989 | Shindo ............... C22C 14/00 148/421 |
| 8,337,750 | B2 | | 12/2012 | Jablokov et al. |
| 2004/0244888 | A1 | * | 12/2004 | Horimura ............ C22C 14/00 148/670 |
| 2009/0017087 | A1 | | 1/2009 | Byon et al. |
| 2009/0062102 | A1 | | 3/2009 | Borrelli et al. |
| 2014/0338795 | A1 | | 11/2014 | Gloriant et al. |
| 2015/0034216 | A1 | * | 2/2015 | Chai .................. C22F 1/183 148/557 |

FOREIGN PATENT DOCUMENTS

| DE | 69008507 T2 | 8/1994 |
| DE | 69631737 T2 | 2/2005 |
| EP | 0992599 A1 | 4/2000 |
| EP | 1143867 A1 | 10/2001 |
| EP | 1211993 | 6/2002 |
| EP | 1726669 A1 | 11/2006 |
| JP | H1136029 | 2/1999 |
| JP | 2011153350 A | 8/2011 |
| JP | 2014029009 | 2/2014 |
| JP | 2015503025 | 1/2015 |
| RU | 2464333 | 10/2012 |
| WO | 2014143983 A1 | 9/2014 |

OTHER PUBLICATIONS

Elias, C. N., et al. "Biomedical applications of titanium and its alloys." Jom 60.3 (2008): 46-49.*
Oldani et al, "Titanium as a Biomaterial for Implants", In: :Recent Advances in Arthroplasty, edited by Dr. Samo Fokter, Jan. 27, 2012 (Jan. 27, 2012), InTech, XP055215780, ISBN: 978-9-53-307990-5, D0I: 10.5772/27413, 15 pages.
Sidel'nikov A.I., "Comparative characteristics of materials groups of titanium used in the manufacture of modem dental implants", InfoDENT, www.divadent.ru, 2000, 4 pages.

* cited by examiner

*Primary Examiner* — Jessee R Roe
(74) *Attorney, Agent, or Firm* — Andrew M. Calderon; Roberts Calderon Safran & Cole, P.C.

(57) ABSTRACT

The disclosure relates to a titanium alloy, in particular to be used for biocompatible implants, which contains no aluminum (Al), vanadium (V), cobalt (Co), chromium (Cr), nickel (Ni) and tin (Sn) and contains at least the following alloy components in wt % in addition to inevitable trace amounts of impurities contained in the alloy components or absorbed during the production: a) 0.2 to 1.5% oxygen (O), b) 0.1 to 1.5% iron (Fe), c) 0.01 to 2% carbon (C), d) the remainder being titanium (Ti).

3 Claims, 1 Drawing Sheet

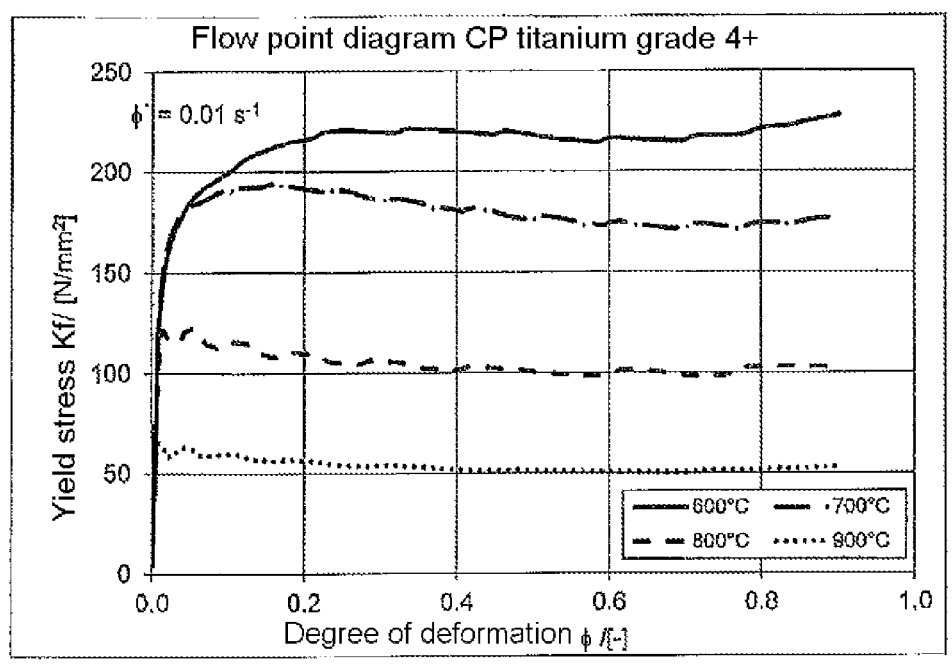

TITANIUM ALLOY

BACKGROUND OF THE INVENTION

Field of the Invention

The invention relates to a titanium alloy having maximum strength that can be used in particular for use for biocompatible implants. The alloy, though, is not to be restricted to this field, but instead may also find general usefulness in other applications.

DISCUSSION OF BACKGROUND INFORMATION

Medical engineering commonly resorts to titanium alloys when the intention is to produce medical and/or prosthetic implants therefrom. One metal alloy typically used, for instance, is Ti—Al6-V4, which was in fact developed for the aircraft industry. These alloys were subsequently assumed to be suitable for use as implant materials, since they possess sufficient mechanical strength and appear to possess acceptable biocompatibility values.

It later emerged that many of the materials, when in body fluids, undergo corrosion to a certain extent and consequently release ions which, over a prolonged period of time, may possibly be harmful. DE 690 08 507 T2 in this regard observes an assumption that the corrosive effects of the body fluids are attributable both to chemical and electrochemical events, and corrosion products are formed when certain commonly used metal alloys form ions as a result of corrosion events within the body. Aluminum metal ions, for example, have been associated with Alzheimer's disease, and vanadium, cobalt, nickel, and chromium are suspected of being toxic or carcinogenic.

In general it is usual for implant metal alloys to be passivated. The passivation, however, produces only thin, amorphous protective oxide films, which adhere poorly and which have proven not to be entirely effective in banishing the formation of corrosion products within the body.

EP 1 211 993 B1 discloses a fixing system for bones, featuring a force-transmitting support with an element inserted therein that can be deformed by inward turning of a bone screw. The function of a fixing system of this kind is to join fragments of bone to one another. These systems have shown themselves to be superior to conventional plate and nail systems in clinical application. Materials used for such fixing systems include titanium materials, which are employed on account of their biocompatibility, which is attributable to a thin layer of titanium oxide. As compared with steels or other metallic materials, titanium materials for this purpose also have a suitable profile of properties, particularly in terms of stiffness and strength, to be used in the human body. Employed generally for such purposes are titanium materials of technical purity (CP titanium) grade 1S to 4 or the aforementioned alloys Ti—Al6-V4 or Ti—Al6-Nb7. Other titanium materials, primarily from the class of the metastable β-titanium alloys (Ti—Mo15) and also, occasionally, from the class of the β-titanium alloys (TNZT), have already received medical approval. They are, however, still undergoing trial.

Common to all kinds of pure titanium is a relatively low strength (tensile strength: $R_m \leq 600$ MPa), resulting in relatively thick plates, screws or nails if used in osteosynthesis. For permanent implants, in the knee or hip area, for example, the strength of CP titanium is too low. In osteosynthesis, therefore, the path taken is that of sandwich plates, in which a soft variety of pure titanium is joined form-fittingly to the titanium alloy Ti—Al6-V4, so as to guarantee sufficient strength. In this case, to increase the angular stability of the plates, it is common to use screws, which cut their own thread into the plates on being turned, and thus normally cause damage to an existing layer of titanium oxide. Nor is any remedy provided here by a thicker titanium oxide layer produced by anodizing.

The dissertation by Y. Müller (Diss. ETH Zurich No. 14542 (2002)) revealed investigations showing that even at room temperature, metal ions may reach the surface of a component of this kind, through cracks in the titanium oxide layer. An oxide layer damaged by insertion of a self-cutting thread screw would make it even easier for metal ions to escape. Relative to the use of the alloy in the human body, this would mean that, correspondingly, aluminum ions and/or vanadium ions would be able to enter the circulating blood. Within the human body, there are areas of very low oxygen content. If, in such areas, titanium with a damaged oxide layer is used, it is not possible for a new oxide layer to form, and so renewed passivation of the alloy fails to occur. The suitability of using such titanium alloys, especially as osteosynthesis material, is therefore not entirely ideal.

SUMMARY OF THE INVENTION

On this basis, the intention is to provide a titanium alloy having maximum strength without using alloying elements whose toxicity has already been demonstrated or which are suspected of triggering diseases.

DESCRIPTION OF THE INVENTION

This object is achieved by means of a titanium alloy which, with exclusion of aluminum (Al), vanadium (V), nickel (Ni), chromium (Cr), cobalt (Co), and tin (Sn) as alloying elements, besides unavoidable trace amounts of impurities which are present in the alloying constituents or have been taken up during production, comprises the following alloying constituents in wt %:

a) 0.2 to 1.5% oxygen (O),
b) 0.1 to 1.5% iron (Fe),
c) 0.01 to 2% carbon (C),
d) balance titanium (Ti).

Although trace amounts of impurities can never be avoided, the increase in strength in the case of the pure titanium variety is achieved by using only alloying constituents that are already present in the human body.

Preferably only these constituents are used, and in that case, especially preferably, 0.4 wt % oxygen (O) and/or 0.5 wt % iron (Fe) and/or 0.08 wt % carbon (C).

In the titanium alloy of the invention, however, for the purpose of boosting strength, it is possible additionally to use alloying constituents which have no known adverse effects on the body, such as gold, molybdenum, niobium, silicon, and zirconium, for example.

The fraction of gold (Au) is preferably less than 1 wt % and especially preferably is 0.1 wt %.

Niobium (Nb) is preferably used additionally with a fraction of less than 1 wt %, and especially preferably with a fraction of 0.1 wt %.

Molybdenum (Mo) is preferably used additionally with a fraction of less than 1 wt % and especially with a fraction of 0.1 wt %.

Zirconium (Zr) is preferably used with a fraction of less than 1 wt % and especially with a fraction of 0.1 wt %.

Nitrogen (N) may additionally be used with a fraction of less than 1.5 wt % and especially with a fraction of less than 0.4 wt %, and in that case especially with a fraction of 0.2 wt %.

Silicon (Si) is preferably used with a fraction of less than 0.5 wt % and especially with a fraction of 0.05 wt %.

Hydrogen (H) as well can be used with a fraction of preferably less than 0.2 wt % in the alloy of the invention.

The elements may be present cumulatively in the alloy. Individual elements, however, may also be entirely absent, according to the strength required in the specific application scenario. Fundamentally, however, it is necessary to rule out the use of the elements aluminum (Al), vanadium (V), and tin (Sn), although here of course it cannot be out of the question for these elements, as impurities in other alloying constituents, to be unavoidable and therefore to have to be tolerated as trace element.

The alloy of the invention can be used preferably for an "intelligent implant with interlocking technology" of the kind described, for example, in EP 1 211 993 B1 or EP 1 143 867 B1. The alloy may also be used for producing material for bone screws and bone nails. The alloy, however, is not intended to be confined necessarily to the field of biocompatible implants, but may instead be employed wherever its strength is sufficient for the desired application.

A suitable starting material is CP titanium grade 4, whose approved maximum levels of accompanying elements are laid down in the specification ASTM F-67, which is valid for medical engineering. The table below shows one possible composition of the titanium alloy of the invention, the FIGURES being in wt %:

| Material | Ti | O | Fe | C | Au | Nb | Mo | Zr | N | Si |
|---|---|---|---|---|---|---|---|---|---|---|
| CP Ti grade 4+ | balance | 0.4 | 0.5 | 0.08 | | | | | | |
| Gold-titanium grade 4+ | balance | 0.4 | 0.5 | 0.08 | 0.1 | | | | | |
| Gold-titanium grade 4+ Nb | balance | 0.4 | 0.5 | 0.08 | 0.1 | 0.1 | | | | |
| Gold-titanium variant 1 | balance | 0.4 | 0.5 | 0.08 | 0.1 | 0.1 | 0.1 | | | |
| Gold-titanium variant 2 | balance | 0.4 | 0.5 | 0.08 | 0.1 | 0.1 | 0.1 | 0.1 | | |
| Gold-titanium variant 3 | balance | 0.4 | 0.5 | 0.08 | 0.1 | 0.1 | 0.1 | 0.1 | 0.2 | |
| Gold-titanium variant 4 | balance | 0.4 | 0.5 | 0.08 | 0.1 | 0.1 | 0.1 | 0.1 | 0.2 | 0.05 |

To estimate the appropriate amounts of alloying elements for the planned use scenario, different binary alloys were investigated first of all. As well as the microstructure and the hardness, analysis focused in particular on the impact strength at room temperature of Ti—O (0.2 to 1.5), Ti—Fe (0.2 to 1.5), and Ti—Nb (0.1 to 2) (FIGURES in wt %).

It then emerged that the addition of gold produces, on the one hand, a further solid solution strengthening of the material and, on the other hand, caused a surprisingly grain-refining effect by precipitation of additional particles in the micrometer range, primarily at the grain boundaries. The reason that this is surprising is that the binary Ti—Au phase diagram predicts something different. This effect is probably due to the low solubility of gold in titanium.

Niobium likewise results in a slight additional solid solution strengthening.

On account of possible adverse effects on the human body, the first three alloys in the table above are preferred, despite the fact that the strength is somewhat lower than that of the gold-titanium variants 1 to 4.

The invention resorts to alloying elements which have hitherto been used only rarely, if at all, for titanium alloys. The success which occurred was therefore not predictable. Instead it is necessary to employ all mechanisms which may lead to strengthening, such as solid solution hardening, fine grain hardening or deformation strengthening, for example.

Alloy production on the laboratory scale took place in a plasma electric arc furnace, with trouble-free melting and casting. This was followed by solution annealing under inert gas (Ar 99.998), microstructure analysis, and a hardness test for estimation of the mechanical properties. For the alloy CP—Ti grade 4+, deformation tests (static: degree of deformation=0.9; dynamic: degree of deformation=0.3) were conducted, and showed that the titanium material of the invention is amenable to hot deformation, this being a precondition for its technical use. On account of the degree of deformation of around 0.3 in the dynamic deformation test, which is inherent in the instrumentation, it was not possible to achieve fine grain by recrystallization annealing. On the basis of additional solid solution strengthening and possibly by the formation of a two-phase titanium alloy, however, the strength of the further solution variants described above ought in any case to be greater than the strength of CP—Ti grade 4+.

The table below shows an example of alloy production:

| Element | wt % [target] | 300 g [target] | Master alloys | 300 g [actual] | wt % [actual] |
|---|---|---|---|---|---|
| Titanium | 99.02 (−0.48) | 300.000 | CP titanium grade 4 | 300.003 | 99.02 |
| Oxygen | 0.40 (+0.10) | 1.206 (+0.301) | TiO$_2$ 99.98% | 0.301 | 0.40 |
| Iron | 0.50 (+0.31) | 1.507 (+0.935) | 99.98% | 0.936 | 0.50 |
| Carbon | 0.08 (+0.07) | 0.241 (+0.211) | 99.995% | 0.211 | 0.08 |
| Total | 100.00 | 301.447 | | 301.451 | 100.00 |

As a master alloy, CP—Ti grade 4 from Daido Steel (FJ2-FJ3, Heat No. TN831G) was used as rod material in a diameter of 8 mm. The chemical composition was taken from the corresponding analytical certificate. To increase the oxygen and carbon contents, corresponding powders (TiO$_2$ and graphite) were weighed out and, in order to avoid blowing losses, were packed into a titanium foil which was placed between titanium rods. The titanium content of the titanium foil was 99.6% and was therefore somewhat above the master alloy used. The resultant slight deviations in chemical composition were disregarded. Since the weight of the titanium foil was only 2.22 g in the context of a total weight of 301.45 g, and since the chemical composition of the foil corresponded approximately to that of the CP—Ti grade 4 used, the disregard appears to be acceptable. Iron was added in granular form.

The table below shows the measured hardnesses (method: Vickers HV10/15) and the tensile strengths estimated from them. Shown for comparison are the alloys Ti—Al6-V4, Ti—Al6-V4 ELI, and also the metastable β-titanium alloy Ti—Mo15, in the solution-annealed and quenched state (LG) and also in the precipitation-hardened state (AG).

| Material | HV10/15 | Rm/MPa |
| --- | --- | --- |
| CP-Ti grade 4 | 221 | 570 |
| CP-Ti grade 4+ | 274 | 760 |
| Gold-titanium grade 4+ | 295 | 840 |
| Gold-titanium grade 4+ Nb | 300 | 860 |
| Ti-Al6-V4 | 290-340*) | 820-1000*) |
| Ti-Al6-V4 ELI | 285-330*) | 800-960*) |
| Ti-Mo15 LG | 215 | 550 |
| Ti-Mo15 AG | 429 | 1320 |

*)according to microstructure condition

The hardness of the inventive pure titanium variants CP—Ti grade and gold-titanium grade 4+ is higher by approximately 20% than the hardness of the hardest pure titanium variety CP—Ti grade 4 and only approximately 10% below or at the lower limit of the hardness of the titanium alloys which have primarily been used to date, namely Ti—Al6-V4 and Ti—Al6-V4 ELI.

The table below shows the effect of the deformation temperature (deformation method: rotary kneading, degree of deformation 0.3) and of subsequent recrystallization annealing on the hardness of the CP—Ti grade 4+ material. Five impressions were made (Pos. 1 to 5).

| Material | Pos. 1 | Pos. 2 | Pos. 3 | Pos. 4 | Pos. 5 | HV10/15 |
| --- | --- | --- | --- | --- | --- | --- |
| CP-Ti grade 4+ 600° C. | 271 | 276 | 282 | 279 | 275 | 276 ± 4 |
| CP-Ti grade 4+ 600° C. RK | 262 | 265 | 258 | 262 | 260 | 261 ± 3 |
| CP-Ti grade 4+ 800° C. | 265 | 267 | 263 | 263 | 263 | 264 ± 2 |
| CP-Ti grade 4+ 800° C. RK | 248 | 257 | 258 | 263 | 262 | 258 ± 6 |
| CP-Ti grade 4+ 900° C. | 272 | 270 | 270 | 276 | 279 | 273 ± 4 |
| CP-Ti grade 4+ 900° C. RK | 262 | 262 | 265 | 254 | 281 | 265 ± 9 |

The single FIGURE shows a flow point diagram. The plot is of the quasi-static flow curves of the CP—Ti grade 4+ alloy as a function of the temperature. When a degree of deformation of 0.9 was reached, the test was discontinued. The samples did not fracture. From the flow point diagram it is clearly evident that the CP—Ti grade 4+ alloy investigated is forgeable.

The invention claimed is:

1. A biocompatible implant made of a titanium alloy, which comprises, with exclusion of aluminum (Al), vanadium (V), cobalt (Co), chromium (Cr), nickel (Ni), and tin (Sn) as alloying elements, besides unavoidable trace amounts of impurities which are present in the alloying constituents or have been taken up during production, at least the following alloying constituents in wt %:
    a) 0.2 to 1.5% oxygen (O),
    b) 0.1 to 1.5% iron (Fe),
    c) 0.01 to 2% carbon (C),
    d) less than 0.5% silicon (Si),
    e) at least one of gold (Au), niobium (Nb), molybdenum (Mo), and zirconium (Zr), in the following amounts:
        less than 1% to 0.1% gold (Au),
        less than 1% to 0.1% niobium (Nb),
        less than 1% to 0.1% molybdenum (Mo), and
        less than 1% to 0.1% zirconium (Zr), and
    f) a balance of titanium (Ti).

2. The titanium alloy as claimed in claim 1, further comprising less than 0.4%, nitrogen (N).

3. A biocompatible implant made of a titanium alloy, which comprises, with exclusion of aluminum (Al), vanadium (V), cobalt (Co), chromium (Cr), nickel (Ni), and tin (Sn) as alloying elements, besides unavoidable trace amounts of impurities which are present in the alloying constituents or have been taken up during production, at least the following alloying constituents in wt %:
    a) 0.2 to 1.5% oxygen (O),
    b) 0.1 to 1.5% iron (Fe),
    c) 0.01 to 2% carbon (C),
    d) less than 0.5% silicon (Si),
    e) less than 1% but more than 0.1% gold (Au), and
    f) a balance of titanium (Ti).

* * * * *